United States Patent [19]
Dalla Riva Toma

[11] Patent Number: 6,054,504
[45] Date of Patent: Apr. 25, 2000

[54] BIOSTATIC COATINGS FOR THE REDUCTION AND PREVENTION OF BACTERIAL ADHESION

[75] Inventor: Joan M. Dalla Riva Toma, Piscataway, N.J.

[73] Assignee: Hydromer, Inc., Branchburg, N.J.

[21] Appl. No.: 09/002,220

[22] Filed: Dec. 31, 1997

[51] Int. Cl.[7] .............................. A01N 43/54; C08L 51/00
[52] U.S. Cl. .......................... 523/122; 514/256; 524/500; 524/537; 524/539
[58] Field of Search .......................... 514/256; 523/122; 524/500, 537, 539

[56] References Cited

U.S. PATENT DOCUMENTS 4,973,493  11/1990  Guire ........................................ 427/2

Primary Examiner—Kriellion Sanders
Attorney, Agent, or Firm—Hoffmann & Baron, LLP

[57] ABSTRACT

The present invention relates to biostatic compositions, as well as coatings and methods for preparing biostatic articles using the same. The compositions contain a hydrophilic polymer possessing a functional group which covalently bonds to an amine, thiol, carboxyl, or hydroxyl active group of an antimicrobial agent. The functional group is capable of reacting with and covalently bonding to an antimicrobial agent without effectively reducing antimicrobial property of the antimicrobial agent below its capability of acting as a biostatic agent and without releasing the antimicrobial agent into a solution.

49 Claims, 3 Drawing Sheets

FIG-1 REACTION OF HEXETIDINE WITH A POLYURETHANE POLYISOCYANATE.

FIG-2 REACTION OF HEXETIDINE WITH MALEIC ANHYDRIDE-CONTAINING POLYMER.

FIG-3  REACTION OF HEXETIDINE WITH AN EPOXIDE-CONTAINING POLYMER.

BIOSTATIC COATINGS FOR THE REDUCTION AND PREVENTION OF BACTERIAL ADHESION

BACKGROUND OF THE INVENTION

1. Field of Invention

The present invention relates to biostatic compositions, as well as coatings and methods for preparing biostatic articles using the same.

2. Description of Prior Art

There have been numerous attempts to concentrate antimicrobial, antiseptic or antibiotic agents on the surface of biomaterials or medical devices as a means of reducing the probability of bacterial adhesion and subsequent bacterial infection. Several approaches have been undertaken including (1) the entrapment of active compounds or agents in surface coatings containing polymer layers or matrices, (2) the coupling of active agents to surface polymers or coatings via ionic or other electrostatic forces and (3) the covalent or chemical bonding of active agents to the surface of polymers or materials.

The first approach involves mechanically entrapping agents within a polymer matrix. The agents are generally released by two mechanisms including (a) the dissolution of the polymer material or (b) diffusion of the agent as a result of osmosis. The second approach involves the coupling of agents to polymer materials as a result of an ionic bond or other intermolecular forces of attraction. Intermolecular attractive forces include dipole-dipole, London or dispersion forces, or hydrogen bonding. These attractive forces occur as a result of the electronegativity or charge differences between the polymer molecule and the active agent or agents. The mechanism of release involves desorption of the active agent or agents from the polymer matrix. The third approach involves the covalent binding of agents to polymers surfaces. This includes the joining of the two materials as a result of chemical bond formation. Covalent bonding of antimicrobial agents to polymer matrices affords systems which generally do not release the bound or joined agent under normal physiological conditions. If release of the agent does occur, it is generally as a result of the hydrolysis of a chemical bond.

Attempts have been made to use the first approach by mechanically entrapping agents in a polymer matrix. For example, U.S. Pat. No. 4,603,152 to Laurin and Stupar discloses antimicrobial compositions comprising 30 to 85% polymeric binder and 15 to 70% antimicrobial metal agents or mixtures. The antimicrobial agents form a chain-like structure which releases itself into solutions to create an initial dosage and then provides the pathway for further release of the agents.

U.S. Pat. No. 5,019,096 to Fox et al. relates to a method for preparing an infection-resistant material or medical device comprised of biomedical polymers and an effective amount of antimicrobial agents such as chlorhexidine salts and silver salts. The agents are released in a controlled fashion when the infection-resistant material is in contact with fluids.

U.S. Pat. No. 5,133,090 to Modak and Sampath discloses an antiviral glove which is comprised of an elastomeric material with an inner coating comprised of a chlorhexidine salt and a lubricating agent which delivers the antiinfective agent within 10 minutes of exposure to an aqueous solution.

U.S. Pat. No. 4,853,978 to Stockum and Surgicos is directed to an antimicrobial medical glove possessing an inner coating comprised of a slow releasing antimicrobial agent in a cross-linked starch. The coating affords slow-release of the antimicrobial agent or agents in order to maintain a bacteria-free environment.

The above patents are directed to dissolution or diffusion of the antimicrobial agent into solution.

The second approach mentioned above involves the coupling of agents to polymer materials as a result of the electrostatic interaction of compounds with polymer materials. For example, U.S. Pat. No. 4,769,013 to Lorenz and Creasy relates to materials containing an antimicrobial agent complexed with polyvinylpyrrolidone, which has been rendered insoluble by being complexed with polyurethane. The medical material is capable of releasing the antimicrobial agent upon contact with water.

U.S. Pat. No. 4,381,380 to LaVeen et al. is directed to a thermoplastic polyurethane article treated with iodine for antibacterial use. The polymeric composition is comprised of a partially crosslinked polyurethane which has been complexed with iodine.

Other attempts have been made to use the second approach. U.S. Pat. No. 4,539,239 to Sakamoto and Takagi discloses the use of chemically bound ion-exchange groups, which serve to ionically bind active agents to the surface of biomaterials. This patent also relates to a process for producing a urinary catheter having film forming materials which possesses functional groups capable of being converted into ion-exchange groups. The ion-exchange groups, described as carboxylic acids, then ionically bind with antimicrobial agents. These materials serve to release the agent into surrounding media as a result of changes in external media.

With this second approach, the active agents are bound somewhat loosely via Van der Waals or ionic forces and are readily released into surrounding environments when in contact with solutions.

Attempts have also been made to use the third approach mentioned above to achieve covalent bonding of agents to polymer surfaces. U.S. Pat. Nos. 4,973,493, 5,263,992, and 5,002,582 to Guire and Guire et al. disclose polymers, surfaces and devices which are modified with biocompatible agents, including antimicrobial compounds, whereby the polymer is chemically bound to a surface or device via a chemically linking moiety which is responsive to a photochemical stimulus and whereby the antimicrobial agent is covalently bound to the surface via a different reactive group. The different reactive group is not responsive to the photochemical stimulus. The antimicrobial agents used in these patents include penicillin and lysozyme.

The solid surface and the antimicrobial agent are chemically joined in U.S. Pat. No. 5,263,992 as in the following formula: A-X-B; wherein A is a photochemically responsive group such as a nitrophenylazide derivative or a benzylbenzoyl derivative, X is a linking moiety such as $C_{1-C_{10}}$ alkyl group and B is a thermochemically reactive group such as a nitrophenylhalides, alkylamines, alkylcarboxyls, alkylthiols, alkylaldehydes, alkylmethylimidates, alkylisocyanates, alkylisothiocyanates and alkylhalides. Lysozyme is an enzyme (protein) which dissolves the bacterial cell wall mucopolysaccharides by hydrolyzing the $\beta(1 \rightarrow 4)$ linkages between N-acetyl-D-muramic acid and 2-acetylamino-2-deoxy-D-glucose residues. Penicillin is a broad spectrum $\beta$-lactam antibiotic which inhibits bacterial cell wall synthesis. The above patents, however, require the use of photochemically reactive groups.

In contrast, the present invention provides a polymer-bound antimicrobial moiety which when applied to a surface of an article reduces the probability of microorganism adherence and thus the possibility of infection without the use of photochemical stimulus. The polymer-bound antimicrobial moiety does not release the antimicrobial agent into solution and does not reduce the antimicrobial properties of the antimicrobial agent below its capability of acting as a biostatic agent.

For a better understanding of the present invention, together with other and further objects, reference is made to the following description taken in conjunction with the examples, the scope of which is set forth in the appended claims.

SUMMARY OF THE PRESENT INVENTION

The present invention is a biostatic composition for reducing and preventing bacterial or microbial adhesion. The composition contains (a) a hydrophilic polymer possessing a functional group which covalently bonds to an amine, thiol, carboxyl, or hydroxyl active group of antimicrobial agents; (b) an antimicrobial agent covalently bound to the hydrophilic polymer; (c) a compatible polymer; and (d) a solvent.

The functional group is capable of covalently bonding to an antimicrobial agent without effectively reducing antimicrobial property of the antimicrobial agent below its capability of acting as a biostatic agent and without releasing the antimicrobial agent into a solution.

The hydrophilic polymer can be, but is not limited to, a polyurethane polymer or prepolymer, a maleic anhydride polymer, a maleic anhydride copolymer, a polyol polymer, a polyamine polymer, an acrylate polymer, an acrylate copolymer, an ethylene oxide modified polymer, and an ethylene oxide modified copolymer.

The antimicrobial agent can be any antimicrobial or antimicrobial derivative having an amine, thiol, carboxyl, or hydroxyl reactive group.

The compatible polymer includes homopolymers or copolymers that are chemically compatible with the present composition and do not interfere with biostatic performance. The function of the compatible polymer is to provide increased lubricity as a result of water absorption or to improve the adhesion of the polymers or coatings to the surface of an article.

The solvent can be, but is not limited to, methyl ethyl ketones, N-methylpyrrolidinones, tetrahydrofurans, ethyl lactates, dichloromethanes, chloroforms, ethyl acetates, propylene glycol methyl ethers, propylene glycol methyl ether acetates, alcohols, ethers, esters, aromatics, chlorinated hydrocarbons, hydrocarbons, water and mixtures thereof.

In one preferred embodiment, the present composition further contains at least one additive. The additive can be, but is not limited to, chemically non-reactive antibiotics, chemically non-reactive antiseptics, chemically non-reactive antimicrobial agents, surfactants, metal complexes, plasticizers, dyes, lubricants, stabilizers, rheology modifiers, fragrances, pigments, visualization aids, anti-foam agents, lubricants, anti-thrombogenic agents, bioeffecting agents, and mixtures thereof.

In another preferred embodiment, the invention includes a polymer-bound antimicrobial moiety formed by reacting a hydrophilic polymer with an antimicrobial agent to form a covalent bond therebetween.

The present invention is also a coating for reducing and preventing bacterial adhesion. The coating is formed from a composition containing (a) a hydrophilic polymer possessing a functional group which reacts with and covalently bonds to an amine, thiol, carboxyl, or hydroxyl active group of antimicrobial agents; (b) an antimicrobial agent which covalently bonds to the hydrophilic polymer; (c) a compatible polymer; (d) a solvent; and (e) optionally at least one additive. The solvent in the composition is then evaporated, and thereby leaving behind a biostatic coating.

The present invention is also a method for preparing a biostatic article by (a) preparing a composition containing a hydrophilic polymer possessing a functional group which reacts with and covalently bonds to an amine, thiol, carboxyl, or hydroxyl active group of antimicrobial agents; an antimicrobial agent which covalently bonds to the hydrophilic polymer; a compatible polymer; a solvent; and at least one additive; (b) applying the composition to the surface of the article; (c) allowing the solvent of the composition to dry; and (d) curing the article.

As a result, the present invention advantageously provides a polymer system possessing a covalently or chemically bound antimicrobial agent that does not release itself into solutions and at the same time does not effectively reduce its antimicrobial property below its capability of acting as a biostatic agent.

The present invention also advantageously provides a polymer system which when applied to a surface reduces and prevents microorganism adherence and thus reduces the probability of microbial and bacterial infection.

The present invention also advantageously reduces the coefficient of friction of the surface of medical articles.

The present invention also advantageously provides a polymer system which exhibits reduced bacterial adherence in a bacterial adherence assay without displaying a zone of inhibition.

DETAILED DESCRIPTION OF THE INVENTION

The present invention is a biostatic composition for reducing and preventing bacterial or microbial adhesion. The composition contains (a) a hydrophilic polymer possessing a functional group which reacts with and covalently bonds to an amine, thiol, carboxyl, or hydroxyl active group of antimicrobial agents; (b) an antimicrobial agent covalently bound to the hydrophilic polymer; (c) a compatible polymer; and (d) a solvent. The present compositions are also effective against fungi and yeast.

The functional group of the hydrophilic polymer is capable of reacting with and covalently bonding to an antimicrobial agent without effectively reducing antimicrobial property of the antimicrobial agent below its capability of acting as a biostatic agent and without releasing the antimicrobial agent into a solution. Examples of the functional group include, but are not limited to, isocyanates, isothiocyanates, esters, aldehydes, N-hydroxysuccinimide esters, epoxides, carboxylic esters, tresylates, anhydrides, alkyl halides, carboxylic acids, haloketones, alkenes, alkynes, and acyl chlorides.

The hydrophilic polymer can be, but is not limited to, a polyurethane polymer, a maleic anhydride polymer, a maleic anhydride copolymer, a polyol polymer, a polyamine polymer, an acrylate polymer, an acrylate copolymer, an ethylene oxide modified polymer, and an ethylene oxide modified copolymer.

Polyurethane polymers are derived from polyurethane polyisocyanate prepolymers. The polyurethane polyisocyanate prepolymers can be derived from reacting (i) an aromatic or aliphatic polyisocyanate and (ii) a polyether polyol or polyester polyol or a polyamine. The polyurethane polyisocyanate prepolymers can also be prepared by reacting (i) an aromatic or aliphatic polyisocyanate with (ii) a polyether polyol or a polyester polyol or a polyamine which has been modified with an antimicrobial agent.

Examples of polyether polyols are, but are not limited to, polytetramethylene ether glycol, poly(ethylene glycol), poly (1,2-butanediol), poly(1,2-butylene glycol) or poly (propylene glycol).

Examples of polyester polyols are, but are not limited to, those derived from the condensation of polycarboxylic acids, preferably dicarboxylic acids, such as adipic, sebacic, phthalic, isophthalic, terephthalic, oxalic, malonic, succinic, maleic, cyclohexane-1,2-dicarboxylic, cyclohexane-1,4-dicarboxylic, polyacrylic napthalene-1,2-dicarboxylic, fumaric, itaconic, and similar dicarboxylic acids with polyalcohols, preferably diols such as ethylene glycol, diethylene glycol, pentaglycol, glycerol, sorbitol, triethanolamine, di(beta-hydroxyethyl)ether, similar diols and/or amino-alcohols such as ethanolamine, 3-aminopropanol, 4-aminopropanol, 5-aminopentanol, 1-6-aminohexanol, 10-aminodecanol, 6-amino-5-methylhexanol-1, phydroxymethylbenzylamine etc. Polyesters derived from ring-opening/condensation of lactones with polyfunctional compounds such as any of the aforementioned polyalcohols can also be used.

Examples of polyamines include, but are not limited to, 1,2-diamino-2methylpropane, hexamethylenediamine, 1,2-diaminocylcohexane, 1,7heptanediamine, 1,8-diaminooctane, 1,9-nonanediamine, diaminonaphthalene, polyethyleneimine, poly(allylamine hydrochloride), poly (propylene glycol)bis(2aminopropyl ether), and poly (propyleneglycol)-poly(ethyleneglycol)-poly(propylene glycol)bis(2-aminopropylether).

The polyether, polyester, and polyamine polyols can be modified with an antimicrobial by using standard organic chemistry reactions including nucleophilic, substitution or condensation reactions.

Suitable examples of polyurethane polyisocyanate prepolymers are, but are not limit to, ricinoleic acid glyceride of diphenylmethane diisocyanate (MDI), polytetramethylene ether glycol-diphenylmethane diisocyanate (MDI), polytetramethylene ether glycol-tolylene diisocyanate (TDI), polytetramethylene ether glycol-isophorone diisocyanate (IPDI), poly(1,4-oxybutylene)glycol-diphenylmethane diisocyanate (MDI), poly(1,4-oxybutylene)glycol-tolylene diisocyanate (TDI), poly(1,4-oxybutylene)glycol-isophorone diisocyanate (IPDI), polyethylene glycol-diphenylmethane diisocyanate (MDI), polyethylene glycol-tolylene diisocyanate (TDI), polyethylene glycol-isophorone diisocyanate (IPDI), polycaprolactone-diphenylmethane diisocyanate (MDI), polycaprolactone-tolylene diisocyanate (TDI), polycaprolactone-isophorone diisocyanate (IPDI), polyethylene adipate-diphenylmethane diisocyanate (MDI), polythylene adipate-tolylene diisocyanate (TDI), polyethylene adipate-isophorone diisocyanate (IPDI), polytetramethylene-diphenylmethane diisocyanate (MDI), polytetramethylene-tolylene diisocyanate (TDI), polytetramethylene-isophorone diisocyanate (IPDI), polyethylene polypropylene adipate-diphenylmethane diisocyanate (MDI), polyethylene polypropylene adipate-tolylene diisocyanate (TDI), and polyethylene polypropylene adipate-isophorone diisocyanate (IPDI). The preferred polyurethane polyisocyanates are the ricinoleic acid glyceride of diphenylmethane diisocyanate (MDI) or polytetramethylene ether glycol-diphenylmethane diisocyanate (MDI) prepolymers.

The maleic anhydride polymer and a maleic anhydride copolymer can be poly(styrene-maleic anhydride), poly (methylvinylether-maleic anhydride), poly(ethylene-maleic anhydride), poly(maleic anhydride-octadecene), poly (butadiene-maleic anhydride), poly(vinylacetate-maleic anhydride), or poly(vinylmethylether-maleic anhydride) preferably poly(styrene-maleic anhydride) and more preferably poly(vinylacetate-maleic anhydride).

The acrylate polymer and acrylate copolymer can be poly(ethyl acrylate), poly(ethyl methacrylate), poly(butyl acrylate), poly(butyl methacrylate), poly(methacrylate methylmethacrylate methacrylic acid), poly(acrylic anhydride), poly(methyl methacrylate), poly(methyl methacrylate butyl methacrylate), poly(methyl methacrylate ethyl methacrylate) or poly(trifluoroethyl methacrylate), preferably poly(ethyl acrylate), and more preferably poly (acrylic anhydride).

The ethylene oxide modified polymer and ethylene oxide modified copolymer can be poly(propylene glycol) diglycidyl ether, poly(allylglycidyl ether ethylene glycol), poly (ethylene-glycidyl methacrylate), poly(ethylene-methyl acrylate-glycidyl methacrylate), polybutadiene functionalized with epoxy/hydroxy group, and any glycidyl ether end-capped or modified polymer, preferably polymers end-capped with glycidyl ether, and more preferably polymers modified with glycidyl ether. Polymers possessing an epoxide group can be prepared using a variety of standard chemical techniques including the oxidation of alkenes or the cyclization of halohydrins.

The percentage of the hydrophilic polymer in the composition is from about 0.1 to about 15 wt. %, preferably from about 0.1 to about 6 wt. %, and more preferably from about 0.1 to about 4 wt. %.

The antimicrobial agent can be any antimicrobial or antimicrobial derivative having an amine, thiol, carboxyl, or hydroxyl reactive group.

The preferred antimicrobial agents are derivatives of hexahydropyrimidine. The more preferred antimicrobial agent is hexetidine. Hexetidine is a broad spectrum antimicrobial agent which has found use in topical preparations for skin and body-cavity infections. The mode of activity of hexetidine is unknown; however, it is noted for its ability to block the utilization of thiamine.

Hexahydropyrimidine derivatives may be prepared as described by Murray Senkas in *Journal of the American Chemical Society* (1946) 68, 1611–1613. Typical reactions involve the condensation of substituted amines with formaldehyde followed by reaction with a compound, which possesses an active hydrogen such as nitromethane via a Mannich-type reaction. For example, the preparation of 1,3-bis(2ethylhexyl)-5-amino-5- methylhexahydropyrimidine (Hexetidine) is prepared by the reaction of 2-ethylhexylamine with formaldehyde followed by reaction with nitroethane. The 5-aminohexahydropyrimidine derivative can then be prepared by catalytic hydrogenation using Raney Nickel.

Examples of hexahydropyrimidine derivatives includes, but are not limited to, 1,3-bis(1-methyl-3,5-dioxa-cyclohexyl)-5-amino-5-methylhexahydropyrimidine, 1,3bis(1-methyl-3,5-dioxa-cyclohexyl)-5-amino-5-propylhexahydropyrimidine, 5-nitro-1,3-bis(1,3-diisopropyl)-5-hydroxymethylhexahydropyrimidine, 5-amino-1,3-bis(1,3diisopropyl)-5-hydroxymethylhexahydropyrimidine, 5-amino-1,3-bis(1,3-diisopropyl-5-methylhexahydropyrimidine, 5-amino-1,3-bis(1,3-diisopropyl)-hexahydropyrimidine, and 5-nitro-1,3-bis(methyl)-5hydroxymethylhexahydropyrimidine.

The antimicrobial agents or derivatives having an amine, thiol, carboxyl or hydroxyl reactive group combine with the functional group of the hydrophilic polymer to form covalent bonds. For example, the reaction of an amine with an isocyanate forms a urea bond. Reaction of an amine with an isothiocyanate forms a thiourea. Reaction of an amine with an ester, a carboxylic ester, an N-hydroxysuccinimide ester, a carboxylic acid or an acyl chloride affords an amide linkage. Reaction of an amine with an epoxide, or alkylhalide produces an alkylamine linkage. Reaction of a hydroxyl group with an isocyanate affords a hydroxyurea linkage. Hydroxyl groups combine with esters, carboxylic esters, N-hydroxysuccinimide esters, carboxylic acids or acyl chlorides to produce carboxylic esters.

The percentage of the antimicrobial agent in the composition is from about 0.1 to about 7 wt. %, preferably from about 0.1 to about 1 wt. %, and more preferably from about 0.1 to about 0.5 wt. %.

Examples of compatible polymer include, but are not limited to, homopolymers or copolymers derived from α-olefins, vinyl chlorides, vinylidene chlorides, ethyleneoxides, propyleneoxides, pyrrolidones, vinylpyrrolidones, hydroxyethylmethacrylates, methacrylates, polysaccharides, acrylamides, methacrylamides, peptides, proteins, nylons, silicone derivatives, acrylic acids, methacrylic acids, vinyl acetates, vinyl alcohols, vinyl ethers, celluloses, aromatic diisocyanates, aliphatic diisocyanates, and mixtures thereof. The function of the compatible polymer is to improve the lubricity of the coated article as a result of water absorption and/or to improve the adhesion of the polymers or coatings to the surface of an article.

The solvent can be, but is not limited to, methyl ethyl ketones, N-methylpyrrolidinones, tetrahydrofurans, ethyl lactates, dichloromethanes, chloroforms, ethyl acetates, propylene glycol methyl ethers, propylene glycol methyl ether acetates, alcohols, ethers, esters, aromatics, chlorinated hydrocarbons, hydrocarbons, water and mixtures thereof.

The present composition optionally contains at least one additive. The additive can be, but is not limited to, chemically non-reactive antibiotics, chemically non-reactive antiseptics, chemically non-reactive antimicrobial agents, surfactants, metal complexes, anti-foam agents, pigments, visualization aids, fragrances, dyes, stabilizers, lubricants, rheology modifiers, plasticizers, anti-thrombogenic agents, bioeffecting agents, or mixtures thereof Examples of anti-thrombogenic agents include heparin, streptokinase, tissue plasminogen activator and urokinase. Examples of surfactants and anti-foam agents include alkylphenol alkoxylates, nonionic and ionic glucosides or polyglucosides, alkylammonium sulfates or sulfosuccinates, silicone derivatives or fluorinated alkyl alkoxylates.

The invention also includes a polymer-bound antimicrobial moiety formed by reacting a hydrophilic polymer with an antimicrobial agent to form a covalent bond therebetween.

When subjected to an extraction assay, the polymer-bound antimicrobial moiety cannot be extracted from solutions. Additionally, the polymer-bound antimicrobial moiety is compatible with a number of substrates, including polyurethane, polyvinyl chloride, silicon, latex, nylon, etc.

The ratio of the hydrophilic polymer and the antimicrobial agent is from about 1:1 to about 150:1, preferably from about 1:1 to about 40.1.

Figure 1:
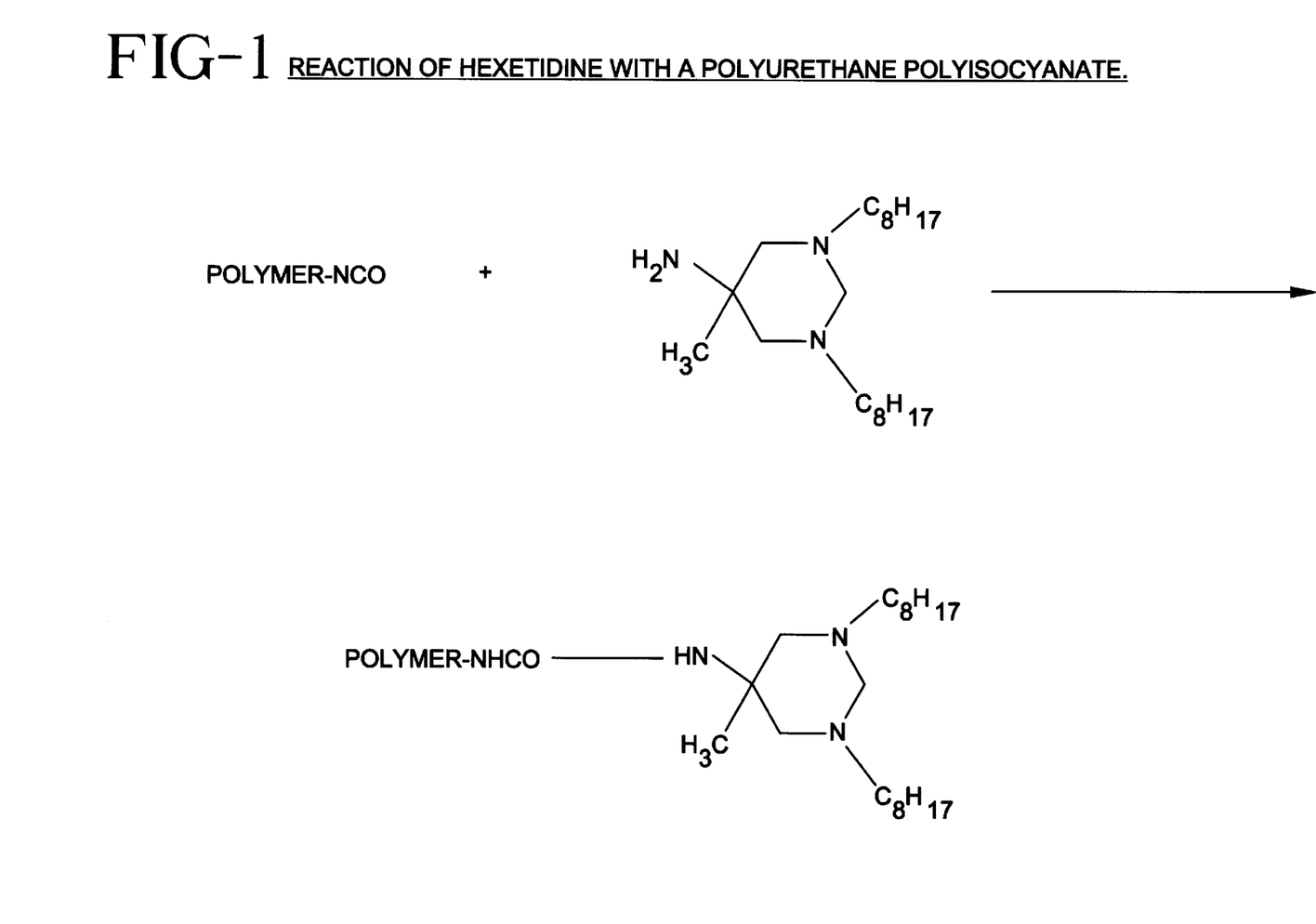
FIG. 1 illustrates a polymer-bound antimicrobial moiety produced by reacting polyurethane polyisocyanate with hexetidine to form a covalent bond via urea linkage.
Figure 2:
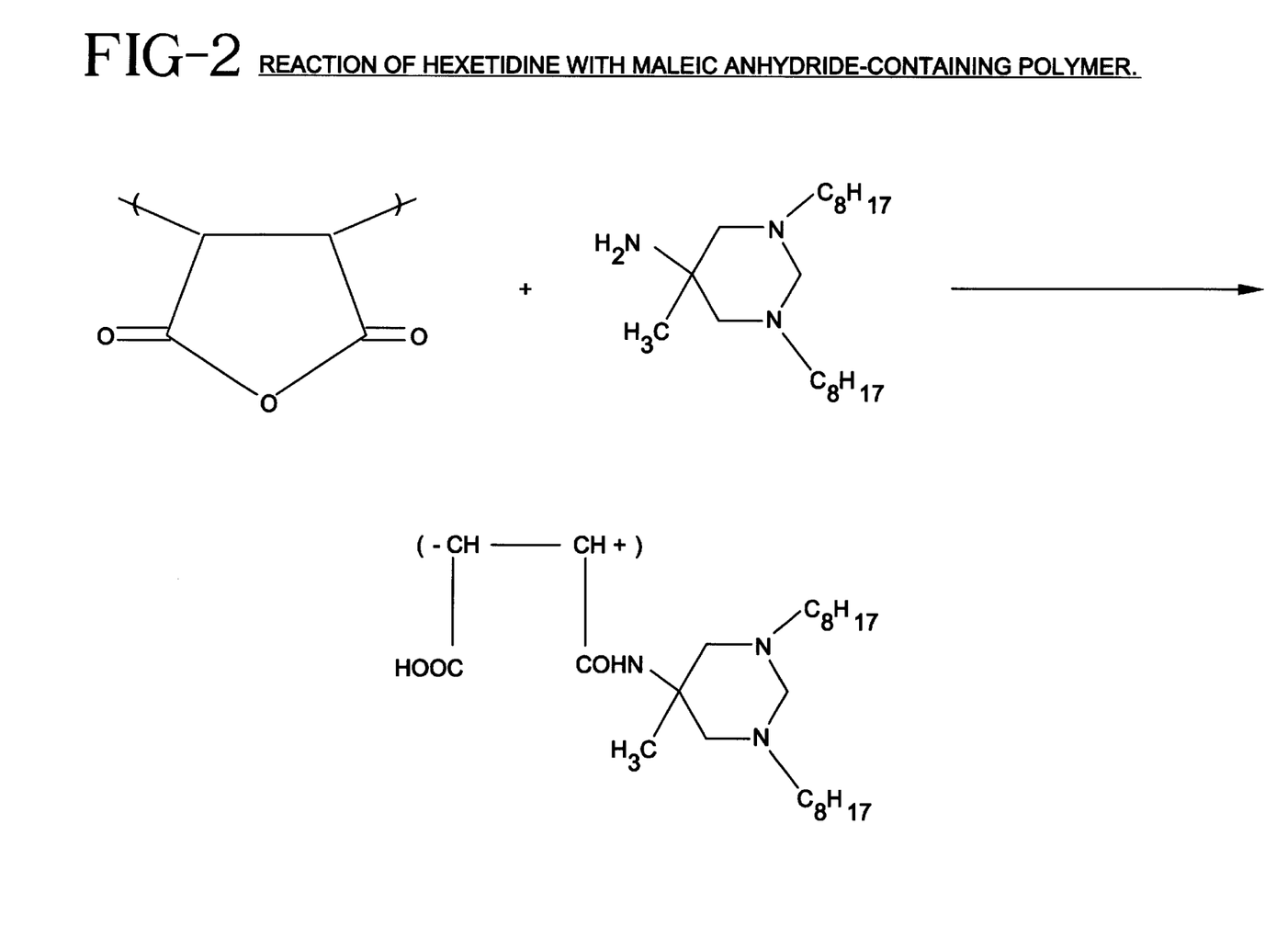
FIG. 2 illustrates a polymer-bound antimicrobial moiety produced by reacting maleic anhydride with hexetidine to form a covalent bond via amide linkage.
Figure 3:
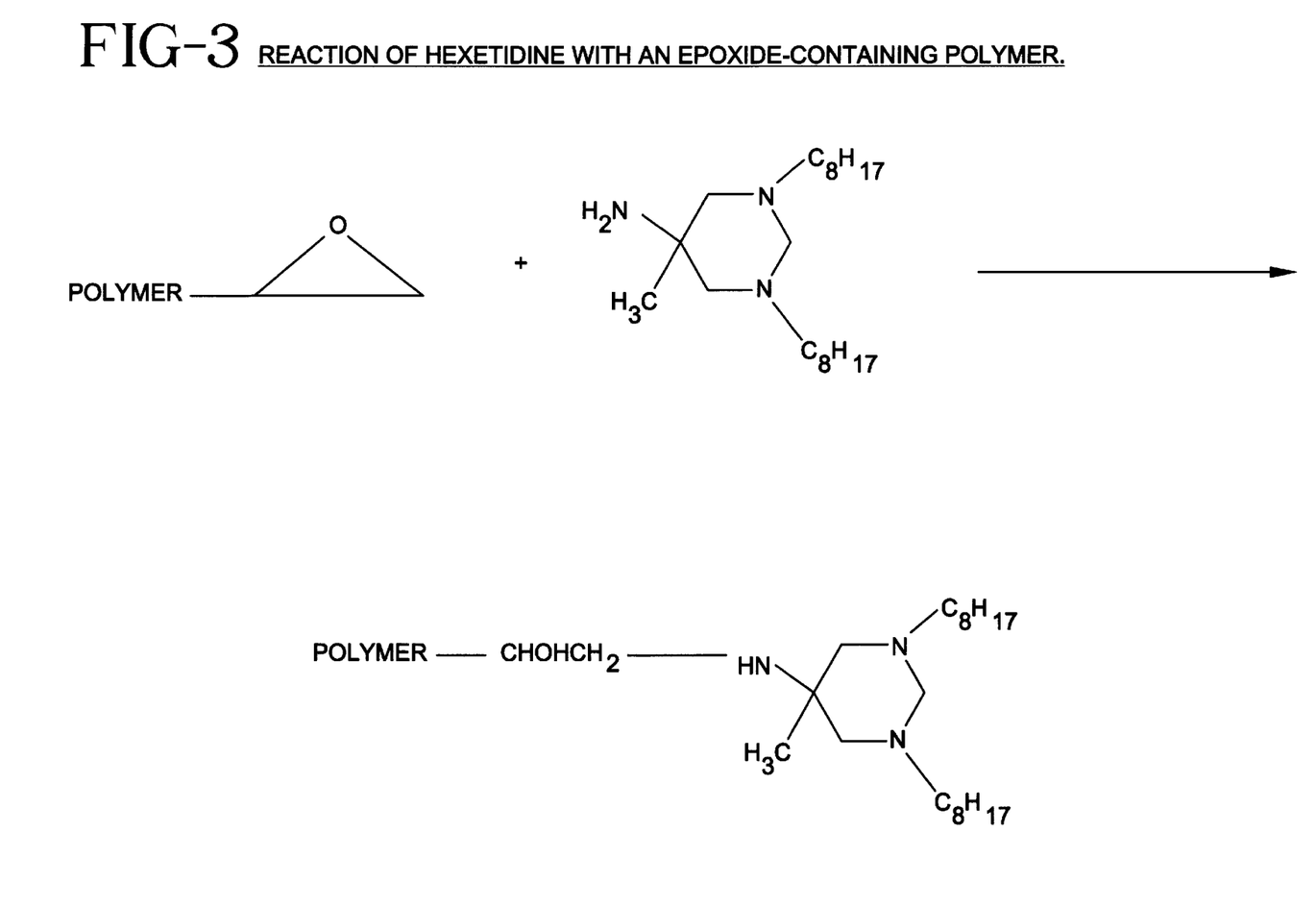
FIG. 3 illustrates a polymer-bound antimicrobial moiety produced by reacting a polymer possessing an epoxy group with hexetidine to form a covalent bond via an alkylamine linkage.

FIG. 1 illustrates the reaction of a polyurethane polyisocyanate with hexetidine to form a polyurethane-bound hexetidine. The covalent bond formed in this case is a urea linkage. FIG. 2 demonstrates the reaction of hexetidine with maleic anhydride. This produces polymer-bound hexetidine. The bond formed between the polymer and hexetidine is an amide bond. FIG. 3 displays the reaction of a polymer possessing an epoxide group with hexetidine. In this case, the polymer-bound hexetidine forms as a result of the alkylation of the primary amine of hexetidine via the epoxide functionality.

The present invention is further a coating for reducing and preventing bacterial adhesion. The coating is formed from a composition containing (a) a coating material comprising a polymer possessing a functional group which reacts with and covalently bonds to an amine, thiol, carboxyl, or hydroxyl active group of antimicrobial agents; (b) an antimicrobial agent covalently bound to said coating material; (c) a hydrophilic polymer; (d) a solvent; and (e) optionally at least one additive. The composition in solution is applied onto a desired substrate to reduce and prevent bacterial adhesion. Once applied, the solvent in the composition evaporates leaving behind a coating containing the hydrophilic polymer covalently bonded to the antimicrobial agent, the compatible polymer and additives.

The composition of the coating contains about 0.3 to about 99% of the hydrophilic polymer; about 0.3 to about 95% of the antimicrobial agent; about 0.3 to about 98% of the compatible polymer; about 0.3 to about 25% of the additives.

The present invention is also a method for preparing a biostatic article by (a) preparing a composition which contains a coating material comprising a polymer possessing a functional group which reacts with and covalently bonds to an amine, thiol, carboxyl, or hydroxyl active group; an antimicrobial agent covalently bound to said coating material; a hydrophilic polymer; a solvent; and at least one additive; (b) applying the composition to the surface of the article; (c) allowing the solvent of the composition to dry; and (d) curing the article. The composition in solution is applied to the article by a manner known in the art, generally by dipping the article into the composition. Once applied, the solvent in the composition is allowed to dry at room temperature for about 5 to about 60 min., or at temperatures of about 40 to about 120° C. for about 5 to about 60 min. After the solvent is dried, the article is cured by a manner known in the art, typically by being placed in an oven for about 5 to about 60 min. at temperature of about 40 to about 120° C.

The article has a substrate that is compatible with the polymer-bound antimicrobial agent. Suitable examples of the substrate are polyurethane, polyvinyl chloride, silicon, latex, nylon, etc.

Preferably, the article is a medical device. Examples of the medical device include, but are not limited to, catheters, guidewires, gloves, contraceptives, wound dressings, drainage tubes, feeding tubes, myringotomy tubes, wound clips, implants, sutures, foams, ophthamalic lenses, prostheses, blood bags, ultrafiltration or dialysis membranes, blood oxygenators, and vascular grafts.

EXAMPLES

The following examples have been set forth below as a guide to the practitioner, and are not meant in any way to limit the scope of the present invention. In the following examples, biostatic compositions containing polymer-bound antimicrobial agents were subjected to biostatic efficacy (zone of inhibition and bacterial adherence), gas chromatographic, infrared, and coefficient of friction analysis. Methodology for such analyses are outlined below.

Biostatic Efficacy Testing Procedures

Biostatic efficacy of the polymer systems was determined using two testing procedures: the zone of inhibition and bacterial adherence analysis. The zone of inhibition is a method which determines the efficacy and extent of releasable antimicrobials. An unreleased chemically bound agent does not exhibit a zone of inhibition, since this method is based on the release of the active agent. The adherence analysis is a method which is based on the adherence of microorganisms to a surface which can result in the formation of a biofilm on the surface. A surface possessing a covalently bound antimicrobial agent demonstrates reduced bacterial adherence in an adherence analysis. A polymeric system which releases an active agent exhibits a zone of inhibition as well as reduced bacterial adherence.

Zone of Inhibition Analysis

The zone of inhibition analysis employed involves a modification of the U.S. Pharmacopeia Procedure for Antibiotics-Microbial Assays. The procedure involved placing the test article (film, tubing, etc.) on an appropriate growth medium which has been seeded with microorganisms. The medium was then incubated for 24 hours at 37° C. The zone diameter was then measured and recorded. An uncoated substrate displayed no zone of inhibition vs. *Staphylococcus aureus* and a substrate coated with 1% ampicillin exhibited a zone of 18 mm.

Bacterial Adherence Analysis

The bacterial adherence assay employed involves incubating the test article in 100 mL of *Staphylococcus aureus* ($10^3$ organisms/mL) in Phosphate Buffer solution for 24 hours at 37° C. with agitation. The test article is removed, washed up to six times in 100 mL of phosphate buffer solution and then incubated in 100 mL of tryptic soy broth at 37° C. for 24 hours. The number of adhering organisms are then determined by U.S. Pharmacopeia Procedure Total Aerobic Microbial Count. An aliquot of the phosphate buffer wash is also plated out to determine the number of viable organisms and to insure complete removal of non-adherent organisms. An uncoated substrate and a substrate coated with 1% Ampicillin served as the control samples. The uncoated substrate exhibited a bacterial adherence of >$3\times10^7$ cfu/mL; the 1% ampicillin sample exhibited a bacterial adherence of <100 cfu/mL.

Gas Chromatographic (GC) Analysis of Polymeric Coatings

GC analysis was performed using a Perkin Elmer AutoSystem Gas Chromatograph equipped with a J & W Scientific DB1 capillary column (30 m×0.32 mm; 0.25 μm) and PE Nelson Model 1022 GC Plus Software. The system operated with temperature programming from 40–160° C. for 18 minutes. The injector temperature operated at 210° C.; the flame ionization detector operated at 250° C. The carrier gas was helium, operating at a pressure of 6.2 psi.

Extraction Assay of Polymeric Coatings

The extraction assay employed involved incubating the test article (films, tubes, etc.) in distilled water or saline (1 gram article per mL of solution) for 24 hours with agitation and determining the presence or absence of the active agent in the extraction media using the GC analysis described earlier.

Infrared Analysis of Polymeric Compositions

Infrared analysis was performed using a Nicolet Impact Series 400D Fourier-Transform Infrared spectrometer equipped with deuterated triglycine sulfate detector, OMNIC software and operating at 4–16 $cm^{-1}$ resolution with Happ-Genzel apodization.

Coefficient of Friction of Biostatic Surfaces

The coefficient of friction of polyvinyl chloride tubing was determined by using a KAYENESS, Inc. material tester equipped with a CHATILLON DFGS Force Gauge and FORCEDAT Data Collection Software from Johnson Scale Co.

Example 1

Comparative Example

A cleaned, uncoated polyvinyl chloride tube was air-dried for 30 minutes and cured at 80° C. for 30 minutes.

The coefficient of friction for the uncoated tube was determined using the method described above. The coefficient of friction was approximately 0.3.

Example 2

Biostatic Composition of the Present Invention

Two grams of the polyurethane polyisocyanate prepolymer (NORDOT Adhesive 34D-2, Synthetic Surfaces, Inc.) prepared by reaction of a 2 molar excess of diphenylmethane diisocyanate (MDI) with ricinoleate polyol, was combined with 250 mg of hexetidine (ANGUS Chemical) in 35 g of methyl ethyl ketone. The reaction was monitored by gas chromatography. Depletion of hexetidine was evident within 8 hours. Infrared analysis displayed the disappearance of the isocyanate peak at approximately 2400 $cm^{-1}$. To the solution was combined 10 g tetrahydrofuran, 10 g N-methylpyrrolidinone, 30 g diacetone alcohol, 3 g polyvinylpyrrolidinone (KOLLIDONE 90 F, BASF). A cleaned polyvinyl chloride tube was dipped in the solution for 15 seconds, air-dried for 30 minutes and cured at 80° C. for 30 minutes.

The tube was examined for bacterial adherence of *S. aureus* using the method described above. An aliquot of both the tryptic soy broth (TSB) and the final phosphate buffer solution (PBS) wash was plated out and displayed no detectable colony formation (<100 cfu/mL). No zone of inhibition was detected using the analysis method outlined above. The coefficient of friction for the coated tube was determined to be approximately 0.075. The presence of hexetidine was not noted in the extraction media.

Example 3

Hydrophilic Composition of the Present Invention

Two grams of the polyurethane polyisocyanate prepolymer (NORDOT Adhesive 34D-2, Synthetic Surfaces, Inc.)

prepared by reaction of a 2 molar excess of diphenylmethane diisocyanate (MDI) with ricinoleate polyol, was combined with 35 g of methyl ethyl ketone, 10 g tetrahydrofuran, 10 g N-methylpyrrolidinone, 30 g diacetone alcohol, 3 g polyvinylpyrrolidinone (KOLLIDON 90F, BASF). A cleaned polyvinyl chloride slide was coated with the solution using a cotton swab. The slide was air-dried for 30 minutes and cured at 80° C. for 30 minutes.

The slide was examined for bacterial adherence of S. aureus using the test procedure described earlier. An aliquot of the TSB was plated out and indicated bacterial adherence (>3×10$^7$ cfu/mL); an aliquot of the final PBS wash was plated out and displayed no detectable colony formation (<100 cfu/mL).

Example 4

Composition of Present Invention

Vorite 3025 polyisocyanate prepolymer (2 g) (CasChem, Inc.) was combined with hexetidine (0.25 g) in methyl ethyl ketone (30 g). The mixture was stirred vigorously overnight. GC analysis indicated the disappearance of hexetidine. Infrared analysis displayed the disappearance of the isocyanate band at 2269 cm$^{-1}$. Tetrahydrofuran (10 g), diacetone alcohol (30 g), N-methylpyrrolidinone (10 g), polyvinylpyrrolidone (3 g; Kollidon 90 F), Fluorinated alkyl alkoxylate (0.1 g; Flourad FC-171) and methyl ethyl ketone (14.65 g) were added to the mixture. The material was then stirred until homogenous.

A polyvinyl chloride (PVC) slide was coated with the solution using a cotton swab saturated with the solution. No bacterial adherence of S. aureus was noted to the coated slide following the bacterial adherence analysis. An aliquot of the PBS wash was plated out and displayed no bacterial adherence. The presence of hexetidine was not noted in the extraction media.

Example 5

Composition of Present Invention

A polyisocyanate prepolymer was prepared by reaction of 4,4-methylenebis(phenylisocyanate) (59 g) with castor oil (72 g) in ethyl methyl ketone (56 g) at 55 C. Two grams of this material were combined with hexetidine (0.25 g) and stirred at room temperature for 8 hours. Tetrahydrofuran (10 g), diacetone alcohol (30 g), N-methylpyrrolidinone (10 g), polyvinylpyrrolidone (3 g) (Kollidon 90 F), Flourad FC-171 (0.1 g) and methyl ethyl ketone (14.65 g) were added to the mixture. The material was then stirred until homogenous.

A PVC slide was coated with the hexetidine derived polymer using a cotton swab saturated with the solution, was air-dried for 30 minutes and cured at 80° C. for 30 minutes. The slide was examined for bacterial adherence of S. aureus using the test procedure described earlier. An aliquot of the TSB and of the final PBS wash was plated out and indicated no bacterial adherence. The presence of hexetidine was not noted in the extraction media.

Example 6

Composition of Present Invention

Polystyrene-co-maleic anhydride copolymer (10 g) was combined with hexetidine (2.2 mL) and triethylamine (0.5 g) in 250 mL of acetone. The mixture was stirred at 40° C. for 1 hour. Infrared analysis displayed the appearance of a new bands corresponding to an amide group (1656 cm$^{-1}$) and a carboxylic acid group (~3500 cm$^{-1}$, 1712 cm$^{-1}$ and 1360 cm$^{-1}$). GC analysis indicated the disappearance of hexetidine.

A PVC slide was coated with the solution using a cotton swab saturated with the solution. No bacterial adherence to the coated slide was noted following the bacterial adherence analysis. The presence of microorganisms was not detected in the PBS wash. The presence of hexetidine was not noted in the extraction media.

Example 7

Composition of Present Invention

A polyol was chemically modified with hexetidine by combining Castor Oil Glycidyl Ether (2.5 g) (Aldrich Chemical Co.) with triethylamine (0.1 g) (Aldrich Chemical Co.) and hexetidine (0.5 g) (Angus). The reaction was monitored by Gas Chromatography and was complete within 30 minutes. To the solution was added methyl ethyl ketone (10 g), a crystal of phosphoric acid and 4,4-methylenebis(phenylisocyanate) (3 g) (Aldrich Chemical Co.). The mixture was stirred for 24 hours whereby infrared analysis exhibited the formation of the polyurethane polyisocyanate prepolymer (NCO~2200 cm$^{-1}$).

To this solution (4.2 g) was added NORDOT Adhesive 34 D-2 (0.6 g), methyl ethyl ketone (42.1 g), tetrahydrofuran (10 g), N-methylpyrrolidinone (10 g) diacetone alcohol (30 g), polyvinylpyrrolidone (KOLLIDON 90 F) (3 g) and Fluorad FC-171 (0.1 g). The mixture was stirred for 24 hours.

A PVC slide was coated with the solution using a cotton swab saturated with the solution. No bacterial adherence of S. aureus to the coated slide was noted following the bacterial adherence analysis. The PBS wash displayed no detectable microorganisms. The presence of hexetidine was not noted in the extraction media.

Thus, while there have been described what are presently believed to be the preferred embodiments, those skilled in the art will appreciate that other and further changes and modifications can be made without departing from the true spirit of the invention, and it is intended to include all such changes and modifications within the scope of the claims which are appended hereto.

What is claimed is:

1. A biostatic composition for reducing and preventing bacterial and microbial adhesion which comprises:
   (a) a hydrophilic polymer possessing a functional group which reacts with and covalently bonds to an active group selected from the group consisting of amine, thiol, carboxyl, and hydroxyl,
   said functional group capable of reacting with and covalently bonding to an antimicrobial agent without effectively reducing antimicrobial property of said antimicrobial agent below its capability of acting as a biostatic agent and without releasing said antimicrobial agent into a solution;
   (b) an antimicrobial agent covalently bound to said functional group of said hydrophilic polymer;
   (c) a compatible polymer; and
   (d) a solvent.

2. The biostatic composition according to claim 1, wherein said functional group of said hydrophilic polymer is selected from the group consisting of isocyanates, isothiocyanates, esters, aldehydes, N-hydroxysuccinimide esters, epoxides, carboxylic esters, tresylates, anhydrides, alkyl halides, carboxylic acids, haloketones, alkenes, alkynes, and acyl chlorides.

3. The biostatic composition according to claim 1, wherein said hydrophilic polymer reacts with and covalently bonds to said antimicrobial agent to form a polymer-bound antimicrobial moiety.

4. The biostatic composition according to claim 1, wherein said hydrophilic polymer is selected from the group consisting of a polyurethane polymer, a maleic anhydride polymer, a maleic anhydride copolymer, a polyol, a polyamine, an acrylate polymer, an acrylate copolymer, an ethylene oxide modified polymer, and an ethylene oxide modified copolymer.

5. The biostatic composition according to claim 4, wherein said polyurethane polymer is polyurethane polyisocyanate derived from reacting (i) an aromatic or aliphatic polyisocyanate with (ii) a polyether polyol.

6. The biostatic composition according to claim 4, wherein said polyurethane polymer is polyurethane polyisocyanate derived from reacting (i) an aromatic or aliphatic polyisocyanate with (ii) a polyester polyol.

7. The biostatic composition according to claim 4, wherein said polyurethane polymer is polyurethane polyisocyanate derived from reacting (i) an aromatic or aliphatic polyisocyanate with (ii) a polyamine.

8. The biostatic composition according to claim 4, wherein said polyurethane polymer is polyurethane polyisocyanate derived from reacting (i) an aromatic or aliphatic polyisocyanate with (ii) a polyether polyol that has been modified with an antimicrobial agent.

9. The biostatic composition according to claim 4, wherein said polyurethane polymer is polyurethane polyisocyanate derived from reacting (i) an aromatic or aliphatic polyisocyanate with (ii) a polyester polyol that has been modified with an antimicrobial agent.

10. The biostatic composition according to claim 4, wherein said polyurethane polymer is polyurethane polyisocyanate derived from reacting (i) an aromatic or aliphatic polyisocyanate with (ii) a polyamine that has been modified with an antimicrobial agent.

11. The biostatic composition according to claim 1, wherein said antimicrobial agent has a reactive group selected from the group consisting of amine, thiol, carboxyl, and hydroxyl.

12. The biostatic composition according to claim 1, wherein said antimicrobial is selected from the group consisting of 1,3-bis(1-methyl-3,5-dioxacyclohexyl)-5-amino-5-methylhexahydropyrimidine, 1,3-bis(1-methyl-3,5-dioxacyclohexyl)-5-amino-5-propylhexahydropyrimidine, 5-nitro-1,3-bis(1,3-diisopropyl)5-hydroxymethylhexahydropyrimidine, 5-amino-1,3-bis(1,3-diisopropyl)-5-hydroxymethylhexahydropyrimidine, 5-amino-1,3-bis(1,3-diisopropyl-5methylhexahydropyrimidine, 5-amino-1,3-bis(1,3-diisopropyl)-hexahydropyrimidine, and 5-nitro-1,3-bis(methyl)-5-hydroxymethylhexahydropyrimidine.

13. The biostatic composition according to claim 1, wherein said antimicrobial is 5-amino-1,3-bis(2-ethylhexyl)-5-methyl-hexahydropyrimidine.

14. The biostatic composition according to claim 1, wherein said compatible polymer is a homopolymer or copolymer derived from the group consisting of α-olefins, vinyl chlorides, vinylidene chlorides, ethyleneoxides, propyleneoxides, pyrrolidones, vinylpyrrolidones, hydroxyethylmethacrylates, methacrylates, polysaccharides, acrylamides, methacrylamides, peptides, proteins, nylons, silicone derivatives, acrylic acids, methacrylic acids, vinyl acetates, vinyl alcohols, vinyl ethers, celluloses, aromatic diisocyanates, aliphatic diisocyanates, and mixtures thereof.

15. The biostatic composition according to claim 1, wherein said solvent is selected from the group consisting of methyl ethyl ketones, N-methylpyrrolidinones, tetrahydrofurans, ethyl lactates, dichloromethanes, chloroforms, ethyl acetates, propylene glycol methyl ethers, propylene glycol methyl ether acetates, alcohols, ethers, esters, aromatics, chlorinated hydrocarbons, hydrocarbons, water and mixtures thereof.

16. The biostatic composition according to claim 1, further comprising at least one additive selected from the group consisting of chemically non-reactive antibiotics, chemically non-reactive antiseptics, chemically non-reactive antimicrobial agents, surfactants, metal complexes, anti-foam agents, pigments, visualization aids, dyes, lubricants, rheology modifiers, fragrances, plasticizers, anti-thrombogenic agents, bioeffecting agents, and mixtures thereof.

17. A coating for reducing and preventing bacterial and microbial adhesion which comprises:
(a) a hydrophilic polymer possessing a functional group which reacts with and covalently bonds to an active group selected from the group consisting of amine, thiol, carboxyl, and hydroxyl,
said functional group capable of reacting with and covalently bonding to an antimicrobial agent without effectively reducing antimicrobial property of said antimicrobial agent below its capability of acting as a biostatic agent and without releasing said antimicrobial agent into a solution;
(b) an anitmicrobial agent covalently bound to said functional group of said hydrophilic polymer; and
(c) a compatible polymer.

18. The coating according to claim 17, wherein said functional group of said hydrophilic polymer is selected from the group consisting of isocyanates, isothiocyanates, esters, aldehydes, N-hydroxysuccinimide esters, epoxides, carboxylic esters, tresylates, anhydrides, alkyl halides, carboxylic acids, haloketones, alkenes, alkynes, and acyl chlorides.

19. The coating according to claim 17, wherein said hydrophilic polymer reacts with and covalently bonds to said antimicrobial agent to form a polymer-bound antimicrobial moiety.

20. The coating according to claim 17, wherein said hydrophilic polymer is selected from the group consisting of a polyurethane polymer, a maleic anhydride polymer, a maleic anhydride copolymer, a polyol, a polyamine, an acrylate polymer, an acrylate copolymer, an ethylene oxide modified polymer, and an ethylene oxide modified copolymer.

21. The coating according to claim 20, wherein said polyurethane polymer is polyurethane polyisocyanate derived from reacting (i) an aromatic or aliphatic polyisocyanate with (ii) a polyether polyol.

22. The coating according to claim 20, wherein said polyurethane polymer is polyurethane polyisocyanate derived from reacting (i) an aromatic or aliphatic polyisocyanate with (ii) a polyester polyol.

23. The coating according to claim 20, wherein said polyurethane polymer is polyurethane polyisocyanate derived from reacting (i) an aromatic or aliphatic polyisocyanate with (ii) a polyamine.

24. The coating according to claim 20, wherein said polyurethane polymer is polyurethane polyisocyanate derived from reacting (i) an aromatic or aliphatic polyisocyanate with (ii) a polyether polyol that has been modified with an antimicrobial agent.

25. The coating according to claim 20, wherein said polyurethane polymer is polyurethane polyisocyanate derived from reacting (i) an aromatic or aliphatic polyisocyanate with (ii) a polyester polyol that has been modified with an antimicrobial agent.

26. The coating according to claim 20, wherein said polyurethane polymer is polyurethane polyisocyanate derived from reacting (i) an aromatic or aliphatic polyisocyanate with (ii) a polyamine that has been modified with an antimicrobial agent.

27. The coating according to claim 17, wherein said antimicrobial agent has a reactive group selected from the group consisting of amine, thiol, carboxyl, and hydroxyl.

28. The coating according to claim 17, wherein said antimicrobial is selected from the group consisting of 1,3-bis(1-methyl-3,5-dioxa-cyclohexyl)-5amino-5-methylhexahydropyrimidine, 1,3-bis(1-methyl-3,5-dioxa-cyclohexyl)-5amino-5-propylhexahydropyrimidine, 5-nitro-1,3-bis(1,3-diisopropyl)-5-hydroxymethylhexahydropyrimidine, 5-amino-1,3-bis(1,3-diisopropyl)-5hydroxymethylhexahydropyrimidine, 5-amino-1,3-bis(1,3-diisopropyl-5-methylhexahydropyrimidine, 5-amino-1,3-bis(1,3-diisopropyl)-hexahydropyrimidine, and 5-nitro-1,3-bis(methyl)-5-hydroxymethylhexahydropyrimidine.

29. The coating according to claim 17, wherein said antimicrobial is 5amino-1,3-bis(2-ethylhexyl)-5-methyl-hexahydropyrimidine.

30. The coating according to claim 17, wherein said compatible polymer is a homopolymer or copolymer derived from the group consisting of α-olefins, vinyl chlorides, vinylidene chlorides, ethyleneoxides, propyleneoxides, pyrrolidones, vinylpyrrolidones, hydroxyethylmethacrylates, methacrylates, polysaccharides, acrylamides, methacrylamides, peptides, proteins, nylons, silicone derivatives, acrylic acids, methacrylic acids, vinyl acetates, vinyl alcohols, vinyl ethers, celluloses, aromatic diisocyanates, aliphatic diisocyanates, and mixtures thereof.

31. The coating according to claim 17, further comprising at least one additive selected from the group consisting of chemically non-reactive antibiotics, chemically non-reactive antiseptics, chemically non-reactive antimicrobial agents, anti-foam agents, pigments, visualization aids, fragrances, dyes, stabilizers, lubricants, rheology modifiers, surfactants, metal complexes, plasticizers, anti-thrombogenic agents, bioeffecting agents, and mixtures thereof.

32. A method for preparing a biostatic article which comprises:
(a) preparing a composition which comprises:
    (i) a hydrophilic polymer possessing a functional group which reacts with and covalently bonds to an active group selected from the group consisting of amine, thiol, carboxyl, and hydroxyl,
    said functional group capable of reacting with and covalently bonding to an antimicrobial agent without effectively reducing antimicrobial property of said antimicrobial agent below its capability of acting as a biostatic agent and without releasing said antimicrobial agent into a solution;
    (ii) an antimicrobial agent covalently bound to said functional group of said hydrophilic polymer;
    (iii) a compatible polymer; and
    (iv) a solvent;
(b) applying said composition to the surface of said article;
(c) allowing said solvent of the composition to dry; and
(d) curing said article.

33. The method according to claim 32, wherein said article is a medical device.

34. The method according to claim 32, wherein said medical device is selected from a group consisting of catheters, guidewires, gloves, contraceptives, wound dressings, drainage tubes, feeding tubes, myringotomy tubes, wound clips, implants, sutures, foams, ophthamalic lens, prostheses, blood bags, ultrafiltration or dialysis membranes, blood oxygenators, and vascular grafts.

35. The method according to claim 32, wherein said functional group of said hydrophilic polymer is selected from the group consisting of isocyanates, isothiocyanates, esters, aldehydes, N-hydroxysuccinimide esters, epoxides, carboxylic esters, tresylates, anhydrides, alkyl halides, carboxylic acids, haloketones, alkenes, alkynes, and acyl chlorides.

36. The method according to claim 32, wherein said hydrophilic polymer reacts with and covalently bonds to said antimicrobial agent to form a polymer-bound antimicrobial moiety.

37. The method according to claim 32, wherein said hydrophilic polymer is selected from the group consisting of a polyurethane polymer, a maleic anhydride polymer, a maleic anhydride copolymer, a polyol, a polyamine, an acrylate polymer, an acrylate copolymer, an ethylene oxide modified polymer, and an ethylene oxide modified copolymer.

38. The method according to claim 32, wherein said polyurethane polymer is polyurethane polyisocyanate derived from reacting (i) an aromatic or aliphatic polyisocyanate with (ii) a polyether polyol.

39. The method according to claim 37, wherein said polyurethane polymer is polyurethane polyisocyanate derived from reacting (i) an aromatic or aliphatic polyisocyanate with (ii) a polyester polyol.

40. The method according to claim 37, wherein said polyurethane polymer is polyurethane polyisocyanate derived from reacting (i) an aromatic or aliphatic polyisocyanate with (ii) a polyamine.

41. The method according to claim 37, wherein said polyurethane polymer is polyurethane polyisocyanate derived from reacting (i) an aromatic or aliphatic polyisocyanate with (ii) a polyether polyol that has been modified with an antimicrobial agent.

42. The method according to claim 37, wherein said polyurethane polymer is polyurethane polyisocyanate derived from reacting (i) an aromatic or aliphatic polyisocyanate with (ii) a polyester polyol that has been modified with an antimicrobial agent.

43. The method according to claim 37, wherein said polyurethane polymer is polyurethane polyisocyanate derived from reacting (i) an aromatic or aliphatic polyisocyanate with (ii) a polyamine that has been modified with an antimicrobial agent.

44. The method according to claim 32, wherein said antimicrobial agent having a reactive group selected from the group consisting of amine, thiol, carboxyl, and hydroxyl.

45. The method according to claim 32, wherein said antimicrobial is selected from the group consisting of 1,3-bis(1-methyl-3,5-dioxa-cyclohexyl)-5amino-5-methylhexahydropyrimidine, 1,3-bis(1-methyl-3,5-dioxa-cyclohexyl)-5-amino-5-propylhexahydropyrimidine, 5-nitro-1,3-bis(1,3-diisopropyl)-5-hydroxymethylhexahydropyrimidine, 5-amino-1,3-bis(1,3-diisopropyl)-5-hydroxymethylhexahydropyrimidine, 5-amino-1,3-bis(1,3-diisopropyl-5-methylhexahydropyrimidine, 5-amino-1,3-bis(1,3-diisopropyl)-hexahydropyrimidine, and 5-nitro-1,3-bis(methyl)-5-hydroxymethylhexahydropyrimidine.

46. The method according to claim 32, wherein said antimicrobial is 5-amino-1,3-bis(2-ethylhexyl)-5-methyl-hexahydropyrimidine.

47. The method according to claim 32, wherein said compatible polymer is a homopolymer or copolymer derived from the group consisting of α-olefins, vinyl chlorides, vinylidene chlorides, ethyleneoxides, propyleneoxides, pyrrolidones, vinylpyrrolidones, hydroxyethylmethacrylates, methacrylates, polysaccharides, acrylamides, methacrylamides, peptides, proteins, nylons, silicone derivatives, acrylic acids, methacrylic acids, vinyl acetates, vinyl alcohols, vinyl ethers, celluloses, aromatic diisocyanates, aliphatic diisocyanates, and mixtures thereof.

48. The method according to claim 32, wherein said solvent is selected from the group consisting of methyl ethyl ketones, N-methylpyrrolidinones, tetrahydrofurans, ethyl lactates, dichloromethanes, chloroforms, ethyl acetates, propylene glycol methyl ethers, propylene glycol methyl ether acetates, alcohols, ethers, esters, aromatics, chlorinated hydrocarbons, hydrocarbons, water and mixtures thereof.

49. The method according to claim 32, further comprising at least one additive selected from the group consisting of chemically non-reactive antibiotics, chemically non-reactive antiseptics, chemically non-reactive antimicrobial agents, anti-foam agents, pigments, visualization aids, lubricants, stabilizers, rheology modifiers, fragrances, dyes, surfactants, metal complexes, plasticizers, antithrombogenic agents, bio-effecting agents, and mixtures thereof.

* * * * *

UNITED STATES PATENT AND TRADEMARK OFFICE
CERTIFICATE OF CORRECTION

PATENT NO. : 6,054,504
DATED : April 25, 2000
INVENTOR(S) : Dalla Riva Toma

It is certified that error appears in the above-indentified patent and that said Letters Patent is hereby corrected as shown below:

Column 5, line 37,   now reads: "methylhexanol-1, phydroxymethylbenzylamine etc."

should read: "methylhexanol-1, p-hydroxymethylbenzylamine etc."-

Column 5, line 42,   now reads: "diaminocylcohexane, 1,7heptanediamine, 1,8-"

should read: "diaminocylcohexane, 1,7-heptanediamine, 1,8-"

Column 6, line 67,   now reads: "1,3-bis(2ethylhexyl)-5-amino-5-"

should read: "1,3-bis(2-ethylhexyl)-5-amino-5-"

Column 7, line 8,   now reads: "cyclohexyl)-5-amino-5-methylhexahydropyrimidine, 1,3bis"

should read: "cyclohexyl)-5-amino-5-methylhexahydropyrimidine, 1,3-bis"

UNITED STATES PATENT AND TRADEMARK OFFICE
CERTIFICATE OF CORRECTION

PATENT NO. : 6,054,504
DATED : April 25, 2000
INVENTOR(S) : Dalla Riva Toma

It is certified that error appears in the above-indentified patent and that said Letters Patent is hereby corrected as shown below:

Column 7, line 12,    now reads: "5-amino-1,3-bis(1,3diisopropyl-5-"

should read: "5-amino-1,3-bis(1,3-diisopropyl-5-"

Column 7, line 16,    now reads: "(methyl)-5hydroxymethylhexahydropyrimidine."

should read: "(methyl)-5-hydroxymethylhexahydropyrimidine."

Column 7, line 62,    now reads: "bioeffecting agents, or mixtures thereof Examples of anti-"

should read: "bioeffecting agents, or mixtures thereof. Examples of anti-"

Column 13, line 54,    now reads: "5methylhexahydropyrimidine, 5-amino-1,3-bis(1,3-"

should read: "5-methylhexahydropyrimidine, 5-amino-1,3-bis(1,3-"

Column 15, line 18,    now reads: "bis(1-methyl-3,5-dioxa-cyclohexyl)-5amino-5-"

should read: "bis(1-methyl-3,5-dioxa-cyclohexyl)-5-amino-5-"

UNITED STATES PATENT AND TRADEMARK OFFICE
CERTIFICATE OF CORRECTION

PATENT NO. : 6,054,504
DATED : April 25, 2000
INVENTOR(S) : Dalla Riva Toma

It is certified that error appears in the above-identified patent and that said Letters Patent is hereby corrected as shown below:

Column 15, line 20,     now reads: "cyclohexyl)-5amino-5-propylhexahydropyrimidine, 5-nitro-"

should read: "cyclohexyl)-5-amino-5-propylhexahydropyrimidine, 5-nitro-"

Column 15, line 23,     now reads: "diisopropyl)-5hydroxymethylhexahydropyrimidine,"

should read: "diisopropyl)-**5-hydroxymethylhexahydropyrimidine,"

Column 15, line 29,     now reads: "antimicrobial is 5amino-1, 3-bis(2-ethylhexyl)-5-methyl-"

should read: "antimicrobial is 5-amino-1, 3-bis(2-ethylhexyl)-5-methyl-"

UNITED STATES PATENT AND TRADEMARK OFFICE
CERTIFICATE OF CORRECTION

PATENT NO. : 6,054,504
DATED : April 25, 2000
INVENTOR(S) : Dalla Riva Toma

It is certified that error appears in the above-identified patent and that said Letters Patent is hereby corrected as shown below:

<u>Column 16, line 62,</u>   now reads: "bis(1-methyl-3,5-dioxa-cyclohexyl)-5amino-5-"

should read: "bis(1-methyl-3,5-dioxa-cyclohexyl)-5-amino-5-"

Signed and Sealed this

Sixth Day of March, 2001

Attest:

NICHOLAS P. GODICI

Attesting Officer    Acting Director of the United States Patent and Trademark Office